(12) United States Patent
Scott

(10) Patent No.: US 6,524,586 B2
(45) Date of Patent: Feb. 25, 2003

(54) ENHANCEMENT OF OLIGOMERIC VIRAL IMMUNOGENICITY

(75) Inventor: Mark D. Scott, Clifton Park, NY (US)

(73) Assignee: Albany Medical College, Albany, NY (US)

( * ) Notice: Subject to any disclaimer, the term of this patent is extended or adjusted under 35 U.S.C. 154(b) by 0 days.

(21) Appl. No.: 09/861,340

(22) Filed: May 18, 2001

(65) Prior Publication Data

US 2002/0172689 A1 Nov. 21, 2002

(51) Int. Cl.$^7$ .................. A61K 39/12; A61K 39/385; A61K 39/39; C12N 7/00
(52) U.S. Cl. ................. 424/196.11; 424/204.1; 424/278.1; 424/280.1; 435/235.1
(58) Field of Search .................. 435/235.1, 238; 424/204.1, 193.1, 194.1, 278.1, 280.1, 281.1, 196.11; 800/8, 21; 530/403

(56) References Cited

U.S. PATENT DOCUMENTS

| | | | |
|---|---|---|---|
| 4,659,569 A | * 4/1987 | Mitsuhashi et al. | 424/194.1 |
| 5,204,243 A | * 4/1993 | Paoletti | 435/235.1 |
| 5,569,468 A | 10/1996 | Modi | |
| 5,908,624 A | 6/1999 | Scott et al. | |
| 5,969,109 A | 10/1999 | Bona et al. | |
| 6,136,321 A | 10/2000 | Barrett et al. | |

FOREIGN PATENT DOCUMENTS

| | | |
|---|---|---|
| JP | 402067227 | 3/1990 |

OTHER PUBLICATIONS

O'Riordan et al (Human Gene Therapy 10:1349–1358, 1999).*

Croyle et al (Journal of Virology 75:4792–4801, May 2001).*

Croyle et al. Human Gene Therapy 11:1713–1722, Aug. 10, 2000.*

Selma Mizouni, Viral Modification with Methoxypol (Ethylene Glycol): Implication for Viral Inactivation and Gene Therapy?, Thesis, Jul. 21, 2000, pp. i–59.

Selma Mizouni, Viral Modification with Methoxypoly(Ethylene Glycol): Implication for Viral Inactivation and Gene Therapy?, Thesis, Jun. 8, 2000, pp. i–59.

Mizouni et al., Viral Modification with Methoxypoly(Ethylene Glycol): Implications for Gene Therapy and Viral Inactivation, 1998, Blood 92 (Suppl. 1), 4627, 1 page.

Mizouni et al., Use of a Two–Phase Partitioning System to Purify an Immunologically Attenuated Viral Vector, 1999, Blood 94 (Suppl. 1) 5081 (415b), 1 page.

* cited by examiner

*Primary Examiner*—Mary E. Mosher
(74) *Attorney, Agent, or Firm*—Schmeiser, Olsen & Watts

(57) ABSTRACT

A method and structure for forming a viral-physiological structure. A naked virus having a capsid is provided. A linker molecule having a covalently attached polymer is covalently bonded to the capsid to form a polymer-protected virus. An immunogenicity of the polymer-protected virus with respect to an animal exceeds an immunogenicity of the naked virus with respect to the animal.

34 Claims, 7 Drawing Sheets

EXAMPLES OF VIRUSES OF HUMAN OR VETERINARY SIGNIFICANCE

| VIRUS | VIRAL FAMILY | HUMAN SIGNIFICANCE | VETERINARY SIGNIFICANCE |
|---|---|---|---|
| Simian Vaculating Virus 40 (SV40) | Polyomaviridae | | + |
| Influenza A/B Viruses | Orthomyxoviridae | + | + |
| Epstein-Barr Virus | Herpesviridae | + | + |
| Rhinoviruses (multiple) | Picornaviridae | + | + |
| Rotaviruses (multiple) | Reoviridae | + | + |
| Respiratory Syncytial Virus | Paramyxoviridae | + | + |
| Adenoviruses (multiple) | Andoviridae | + | + |
| Coxsackievirus (multiple) | Picornaviridae | + | + |
| Coronavirus (multiple) | Coronaviridae | + | + |
| Parainfluenza Virus (multiple) | Paramyxoviridae | + | + |
| Mumps Virus | Paramyxoviridae | + | |
| Hepatitis A Virus | Picornaviridae | + | + |
| Hepatitis B Virus | Hepadnaviridae | + | + |
| Hepatitis C Virus | Flaviviridae | + | + |
| Hepatitis D Virus | 'Viroid-Like' | + | + |
| Hepatitis E Virus | 'Norwalk–Like' | + | + |
| Variola Virus | Poxviridae | + | + |
| Hanta Virus | Hantavirus | + | + |
| Dengue Virus 1-4 | Togaviridae | + | |
| Measles Virus | Paramyxoviridae | + | |
| Rubella Virus | Togaviridae | + | |
| Parvovirus | Parvoviridae | + | |
| Herpes Simplex Virus 1, 2 | Herpesviridae | + | |
| HTLV-I | Retroviridae | + | |
| HTLV-II | Retroviridae | + | |
| Human Immunodeficiency Virus (HIV-1, HIV-2) | Retroviridae | + | |
| Simian Immunodeficiency Virus (SIV) | Retroviridae | | + |
| Papillomavirus | Papovaviridae | + | |
| Poliovirus | Picornaviridae | + | |
| Rabies Virus | Rhabdoviridae | + | + |
| Various Encephalitis Viruses (e.g., Tick-borne, Mosquito-borne; Human, Equine, etc.) | Togaviridae Flaviviridae Bunyaviridae | + | + |
| Feline Leukemia Virus | Parvoviridae | | + |
| Feline Immunodeficiency Virus | Retroviridae | | + |
| Canine Parvovirus | Parvoviridae | | + |
| Canine Distemper Virus | Paramyxoviridae | | + |
| Mucosal Disease Virus (Cattle) | Togaviridae | | + |
| Rift Valley Fever | Bunyaviridae Togaviridae | + | + |
| African Swine Fever Virus | Iridoviridae | | + |
| Marburg Viruses | Filoviridae | + | + |
| Hemorrhagic Viruses (multiple) | Flaviviridae Arenaviridae Bunyaviridae | + | + |

*FIG. 4*

EXAMPLES OF PEG LINKER CHEMISTRY CAPABLE OF VIRAL SURFACE MODIFICATION

| NAME OF POLYMERATED LINKER CHEMICAL (PLC) | TARGET OF PLC |
|---|---|
| aldehyde PEG | Reacts with Primary Amines |
| w-amino-a-carboxyl PEG | Protein Amino Groups |
| benzotriazole carbonate | Protein Amino Groups (primarily lysine) |
| carbonylimidazole PEG | Protein Amino Groups |
| cynauric chloride PEG | Protein Amino Groups (primarily lysine) |
| epoxide PEG | Amino, Hydroxyl, and Thiol groups |
| glycidyl ether (epoxide) of PEG | Amino, Hydroxyl, and Thiol groups |
| isocyanate PEG | Alcohol Groups and Amines |
| maleimide PEG | Thiol Groups |
| N-hydroxysuccinimidyl-maleimide (NHS-maleimide) | Amine and Thiol Groups |
| NHS-vinylsulfone | Amine and Thiol Groups |
| NHS-PEG2 | Amine and Thiol Groups |
| p-nitrophenylcarbonate PEG | Protein Amino Groups |
| oxycarbonylimidazole PEG | Amine Groups |
| orthopyridyl disulfide | Thiol Groups |
| phospholipid PEG | Intercalates into Lipid Membrane/Capsid Surfaces (no covalent bonding) |
| succinimidyl butanoate (SBA-PEG) | Lysine and Terminal Amines |
| succinimidyl ester of carboxymethylated PEG | Lysine and Terminal Amines |
| succinimidyl propionate (SPA-PEG) | Lysine and Terminal Amines |
| succinimidyl succinamide (SSA-PEG) | Lysine and Terminal Amines |
| succinimidyl succinate PEG (SS-PEG) | Amine Groups |
| thiol PEG | Thiol Groups |

US 6,524,586 B2

ENHANCEMENT OF OLIGOMERIC VIRAL IMMUNOGENICITY

BACKGROUND OF THE INVENTION

1. Technical Field

The present invention relates to covalent modification of surface protein or carbohydrate of a virus for enhancing immunogenicity of the virus.

2. Related Art

A vaccine inoculation administered to a person may comprise a live attenuated virus (e.g., a polio virus) for eliciting an immune response that enables the person to develop an immunity to being subsequently infected by the virus. Although the vaccine may be effective for a majority of people so inoculated, unfortunately a small percentage of people so inoculated actually develop the viral disease associated with the virus. Thus, it is desirable to maintain or enhance the effectiveness of the vaccine for immunization purposes, while at the same time reduce or eliminate the risk of contracting the viral disease as a result of being inoculated by the vaccine.

SUMMARY OF THE INVENTION

The present invention provides a method for forming a viral-physiological structure, comprising:

providing a naked virus having a capsid; and covalently bonding a linker molecule to the capsid, wherein a polymer is covalently attached to the linker molecule to form a polymer-protected virus, and wherein an immunogenicity of the polymer-protected virus with respect to an animal exceeds an immunogenicity of the naked virus with respect to the animal.

The present invention provides a viral-physiological structure, comprising:

a naked virus having a capsid; and means for covalently bonding a linker molecule to the capsid, wherein a polymer is covalently attached to the linker molecule to form a polymer-protected virus, and wherein an immunogenicity of the polymer-protected virus with respect to an animal exceeds an immunogenicity of the naked virus with respect to the animal.

The present invention provides a viral-physiological structure, comprising:

a naked virus having a capsid; and a linker molecule covalently bonded to the capsid, wherein a polymer is covalently attached to the linker molecule to form a polymer-protected virus, and wherein an immunogenicity of the polymer-protected virus with respect to an animal exceeds an immunogenicity of the naked virus with respect to the animal.

The present invention maintains or enhances the effectiveness of a vaccine for immunizing a person or non-human animal to viral disease associated with a virus, while at the same time reduces or eliminates the risk of contracting the viral disease as a result of being inoculated by the vaccine.

BRIEF DESCRIPTION OF THE DRAWINGS

FIG. 4 lists exemplary viruses of human significance and of veterinary significance, in accordance with embodiments of the present invention.

FIG. 6 lists exemplary polymerated linker compounds and associated protein or carbohydrate targets that can be reacted with the exemplary polymerated linker compounds, for use in conjunction with FIGS. 1 and 3, and in accordance with embodiments of the present invention.

DETAILED DESCRIPTION OF THE INVENTION

Figure 1:
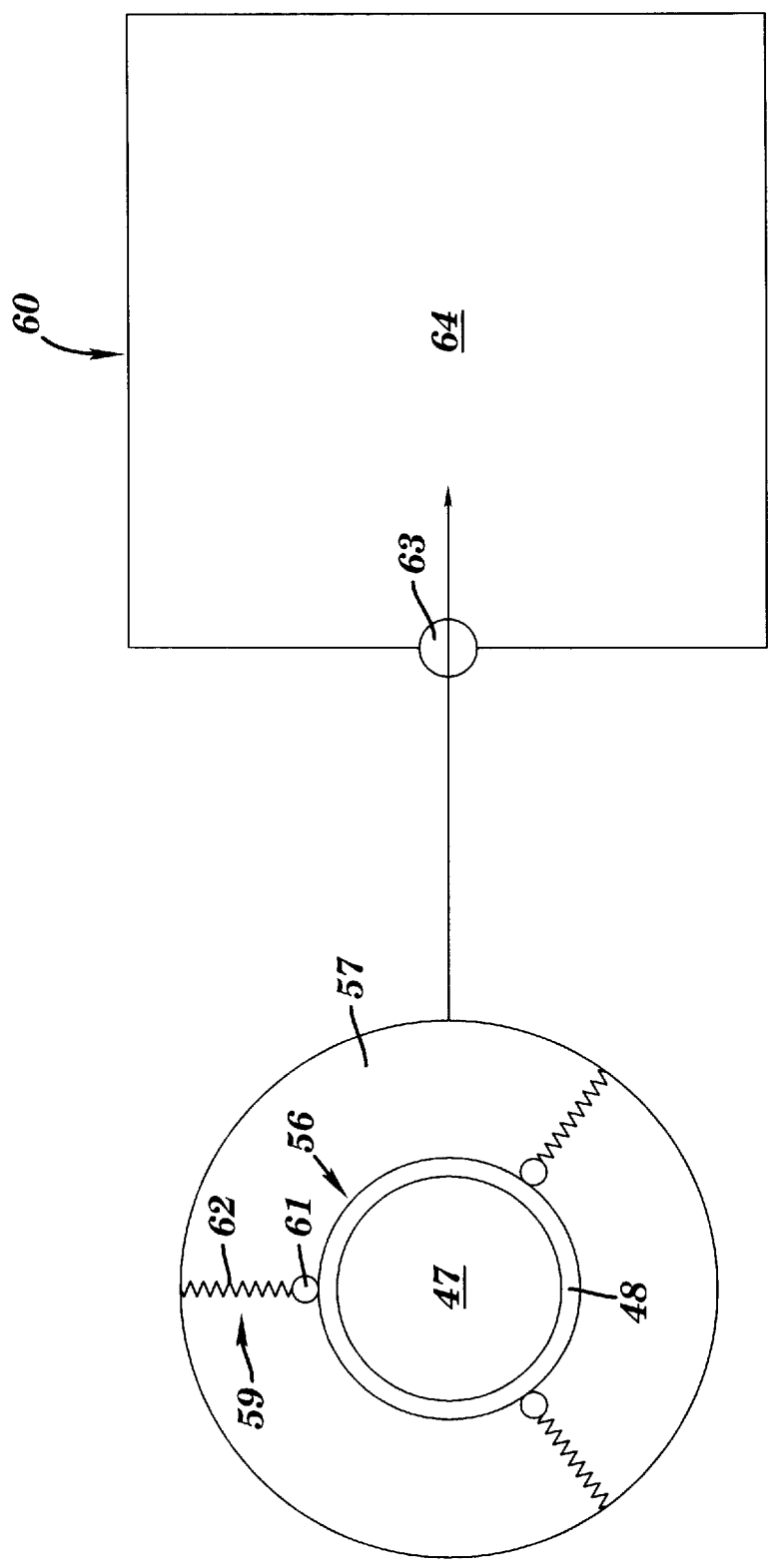
FIG. 1 depicts a cross-sectional view of a virus within a blocker envelope that envelops the virus, and entry of the virus into an animal, in accordance with embodiments of the present invention.

FIG. 1 depicts a cross-sectional view of a virus 56 and a blocker envelope 57 that envelops the virus 56, and entry of the virus 56 into an animal 60, in accordance with embodiments of the present invention. The virus 56 includes a viral core 47 and a capsid 48. The viral core 47 includes genetic material (i.e., DNA or RNA). The capsid 48 is a shell comprising protein. Some viruses additionally include an outer lipid envelope (not shown) that surrounds the capsid. The virus 56 may be a live virus or a dead virus. A live virus is defined herein as a virus whose genetic material is sufficiently intact that the virus is capable of replication when within a host cell. A dead virus is what remains of a previously existing live virus, wherein the what remains is not capable of replication when within the host cell.

The animal 60 may be a human animal (e.g., a human being or a fetus) or a veterinary animal. A veterinary animal is a non-human animal of any kind such as, inter alia, a domestic animal (e.g., dog, cat, etc.), a farm animal (cow, sheep, pig, etc.), a wild animal (e.g., a deer, fox, etc.), a laboratory animal (e.g., mouse, rat, monkey, etc.), an aquatic animal (e.g., a fish, turtle, etc.), etc.

The blocker envelope 57 results from covalent bonding of a polymerated linker chemical 59 with the virus 56. The polymerated linker chemical 59 includes a linker molecule 61 with a covalently attached polymer 62. The polymerated linker chemical 59 is said to represent an activated form of the polymer 62. For example, if the polymer is methoxy-polyethylene glycol (mPEG), then then "activated mPEG" is exemplified by having mPEG covalently bonded to the linker molecule of cyanuric chloride. As another example, if the polymer is polyethylene glycol (PEG), then then "activated PEG" is exemplified by having PEG covalently bonded to the linker molecule of cyanuric chloride. The linker molecule 61 is covalently bonded to proteins or carbohydrates in an outer portion (i.e., the capsid 48) of the virus 56. The covalent linking of the linker molecule 61 to a protein may include a covalent linking of the linker molecule 61 to an amino acid in the protein or to a sulfhydryl group in the protein. The polymer 62 has a "long chain length;" i.e., a chain length that is of sufficient magnitude to fill the space around itself to create the blocker envelope 57. Thus if the virus 56 is within the animal 60, then the blocker envelope 57 constitutes a barrier that protects the virus 56 from being easily removed or destroyed by white blood cells (e.g., phagocytes) that might otherwise engulf and destroy the virus 56, or from being precipitated out of the bloodstream of the animal 60. In addition, the polymer 62 within the blocker envelope 57 inhibits, by steric hindrance, the removal or destruction of the virus 56. Additionally, the polymer 62 may be highly hydrophillic so as to create a hydration zone around itself to alternatively create the blocker envelope 57.

As will be discussed infra, the ability of the blocker envelope 57 to prevent early or "premature" removal of the virus 56 from the bloodstream of the animal 60 enhances the immunogenicity of the virus 56 with respect to the animal 60. The present invention discloses how the enhanced immunogenicity of the virus 56 may be utilized to make a vaccine that is more effective and safer than corresponding vaccines of the related art. Definitionally, an immunogenicity of the virus 56 with respect to the animal 60 is an ability of the virus 56 to evoke an immune response within the animal 60 at any time that the virus 56, or fragments thereof, is within the animal 60. Invoking an immune response within the animal 60 means production by the animal 60 of antibodies in response to the virus 56 and, typically, production by the animal 60 of antibodies to protein components within the capsid of the virus 56. Note that the immunogenicity of a virus is always relative to a specific animal species, inasmuch as the virus may be more immunogenic when within a first animal species (e.g., a cow) than when within a second animal species (e.g., a mouse), and the virus may be non-immunogenic when within a third animal species (e.g., a human being). An "enhancement" of the immunogenicity of the virus 56 means a statistically significant increase in the ability of the virus 56 to evoke an immune response within the animal 60 at any time that the virus 56, or fragments thereof, is within the animal 60. Immunogenicity, or of enhancement of immunogenicity, may be determined or confirmed by measurement of antibody formation by the animal 60 in response to presentation of the virus 56 to the immune system of the animal 60. Note that introducing the virus 56 into the animal 60 may stimulate production of antibodies but does not necessarily immunize the animal 60. Immunization requires that the quantity of the virus 56 that is introduced into the animal 60 be sufficient to immunize the animal 60 against infection by the virus 56.

The blocker envelope 57 may be formed around the virus 56 by any suitable method for bonding the polymerated linker chemical 59 to the virus 56, such as, inter alia, spraying the polymerated linker chemical 59 onto the virus 56, immersing the virus 56 into a liquid medium that includes the polymerated linker chemical 59, reacting the polymerated linker chemical 59 with the virus 56 with further processing to create a pill that includes the polymerated linker chemical 59 enveloped around the virus 56, etc.

In FIG. 1, the virus 56 together with its enveloping blocker envelope 57 enters the animal 60 through an entry 63. The entry 63 denotes any entry into the animal 60 into which, or through which, the virus 56 may enter the animal 60. The virus 56 may enter the animal 60 through the entry 63 by any method or mechanism that is known to one of ordinary skill in the art for introducing a virus into an animal, as illustrated by the following examples As a first example, the entry 63 may be a mouth into which the virus 56 enters in pill, liquid, or spray form. As a second example, the entry 63 may be a nose into which the virus 56 enters by a nasal spray. As a third example, the entry 63 may be a blood vessel into which the virus 56 enters by transfusion or injection. As a fourth example, the entry 63 may be a muscle into which the virus 56 enters by needle injection. As a fifth example, the entry 63 may be a vagina (if the animal 60 is female) into which the virus 56 enters via use of a syringe.

Figure 2:
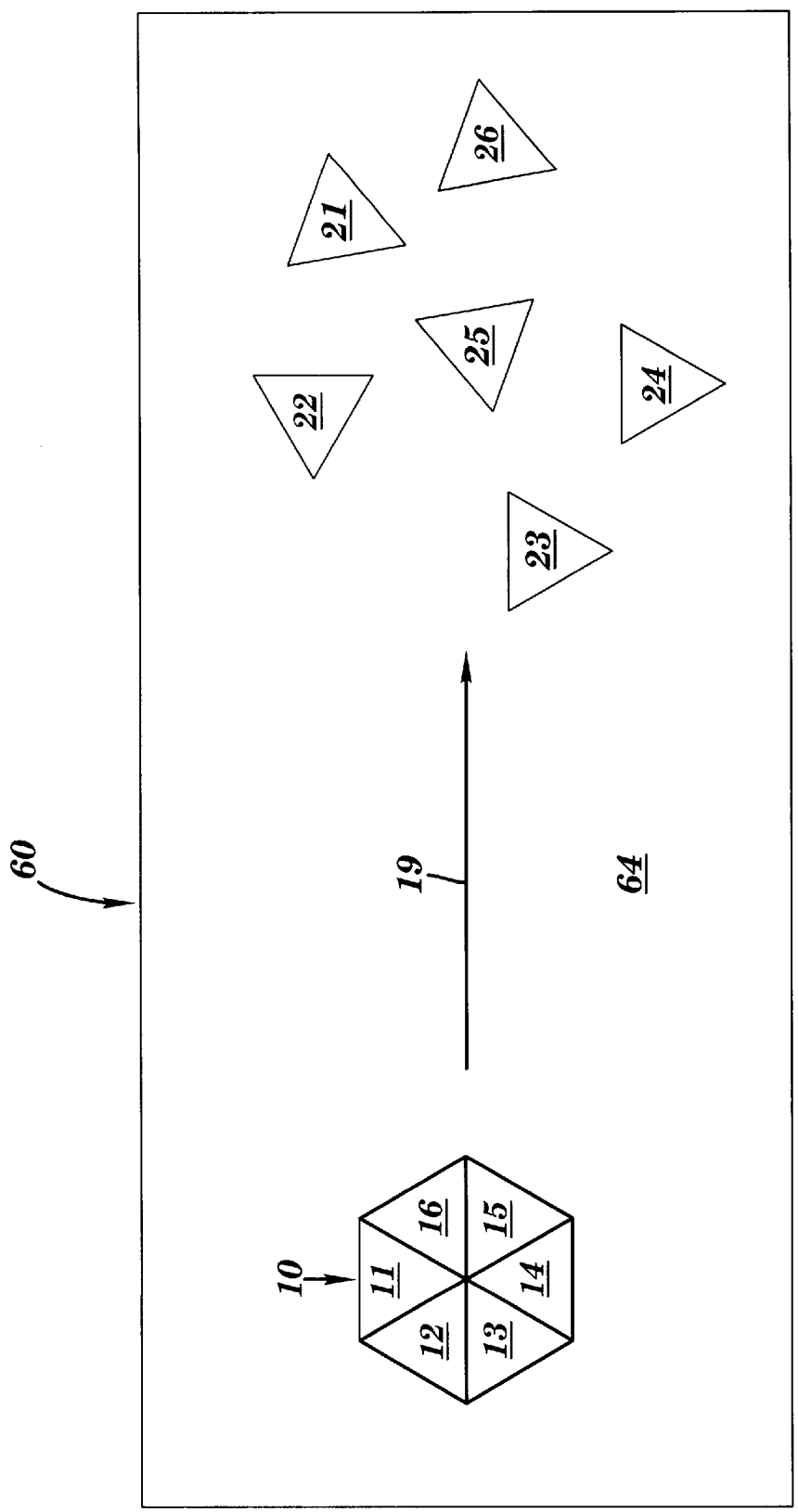
FIG. 2 depicts a top view of a virus before and after the virus has fissioned into viral fragments.

FIG. 2 depicts a top view of a virus 10 within the animal 60 of FIG. 1. The virus 10 may be introduced into, or caused to enter, the animal 60 by any method or mechanism discussed supra for causing the virus 56 to gain entry into the animal 60 in FIG. 1. In FIG. 2, the virus 10 has an oligomeric composition (i.e., a composition having two or more subunits) comprising viral structural units 11, 12, 13, 14, 15, and 16. Noting that the virus 10 is unstable, the virus 10 will experience a spontaneous fission (i.e., falling apart) transformation 19 into viral fragments 21, 22, 23, 24, 25, and 26 respectively corresponding to the viral structural units 11, 12, 13, 14, 15, and 16. Each of the viral fragments 21, 22, 23, 24, 25, and 26 may potentially evoke an immune response in the animal 60, provided that the virus 10 has presented itself to the immune system of the animal 60 for a period of time long enough for the immune system of the animal 60 to become immunologically sensitive to the virus 10. The immune system of the animal 60 has become immunologically sensitive to the virus 10 when said immune system produces a statistically significant quantity of antibodies in response to the virus 10. As discussed supra, the immunogenicity of the virus 10 includes the ability of the viral fragments 21, 22, 23, 24, 25, and 26 to evoke an immune response from the animal 60.

Notwithstanding an intended use of the virus 10 for immunological purposes, the animal 60 initially views the virus 10 as a foreign particle and attempts to remove or render non-viable the virus 10 as quickly as possible such as by enlisting a white blood cell (e.g., a phagocyte) to engulf and consume the virus 10. Alternatively, the virus 10 may precipitate out of solution soon after its entry into the bloodstream of the animal 60. Thus, the virus 10 may be "prematurely" removed from the animal 60 with consequent poor presentation of the virus 10 to the immune system of the animal 60. "Prematurely" means prior to attainment by the animal 60 of the requisite immunological sensitivity, as defined supra. Consequently, the virus 10 may not endure long enough for the immune system of the animal 60 to develop said immunologically sensitivity to the virus 10.

A vaccine may comprise a collection of such viruses 10, and each such virus 10 of the collection fissions at a different point in chronological time even if each virus 10 of the collection is introduced into the animal 60 at the same initial time. Consequently, a substantial portion of the viruses 10 of the collection will be removed or rendered ineffective before the animal 60 has become immunologically sensitive or before the viruses 10 fissions into the viral fragments 21, 22, 23, 24, 25, and 26. Thus, in order to render the vaccine immunologically effective, the virus 10 dosage may have to be increased to a level that compensates for those viruses that have been prematurely removed, which increases the risk of the animal 60 being actually infected by a live virus of the same type as the virus 10 and thereby acquiring the disease associated with the infection.

Figure 3:
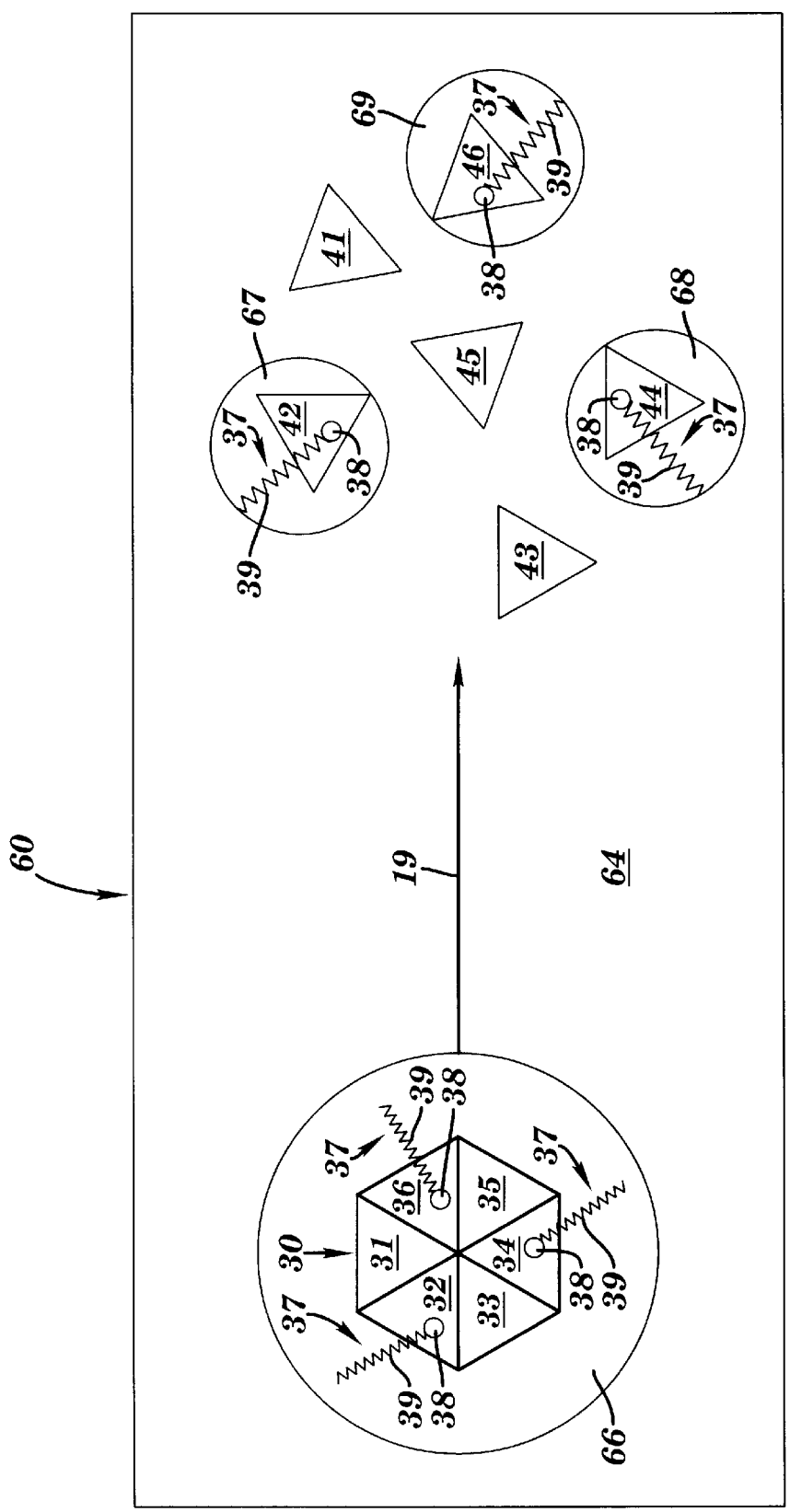
FIG. 3 depicts a top view of a virus that is enveloped by a blocker envelope before and after the virus has fissioned into viral fragments, in accordance with embodiments of the present invention.

FIG. 3 depicts a top view of a virus 30 within the animal 60 of FIG. 1, in accordance with the present invention. The virus 30 may be introduced into, or caused to enter, the animal 60 by any method or mechanism discussed supra for causing the virus 56 to gain entry into the animal 60 in FIG. 1. In FIG. 3, the virus 30 has an oligomeric composition comprising viral structural units 31, 32, 33, 34, 35, and 36. Unlike the virus 10 of FIG. 2, the virus 30 of FIG. 3 is covalently bonded to a polymerated linker chemical 37, which creates a blocker envelope 66 that envelops the virus 30. In particular, each of the viral structural units 32, 34, and 36 of the virus 30 of FIG. 3 are covalently bonded to the polymerated linker chemical 37 at a viral capsid of the virus 30 (not shown in FIG. 3, but illustrated for capsid 48 of the virus 56 of FIG. 1). In FIG. 3, the polymerated linker chemical 37 comprises a polymer 39 covalently bonded to a linker molecule 38, and the linker molecule 38 is covalently bonded to the viral capsid of the virus 30.

The virus 30 of FIG. 3 exemplifies a "polymer-protected" virus, while the virus 10 of FIG. 1 exemplifies a "naked virus". A "polymer-protected" virus is a virus that is enveloped by a blocker envelope, while a "naked virus" is a virus that is not enveloped by a blocker envelope.

Due to protection provided by the blocker envelope 66, the virus 30 of FIG. 3 is not subject to premature removal from the animal 60 for the same reasons, discussed supra, that the virus 56 is not subject to premature removal from the animal 60 in FIG. 1 in light of the blocker envelope 57 around the virus 56 of FIG. 1. Additionally, the polymer 39 the polymerated linker chemical 37 keeps the virus 30 in solution within the vascular system of the animal 60 so that the virus 30 does not readily precipitate out of solution. Accordingly, the blocker envelope 66 increases the average "survival time" of the virus 30 in the bloodstream of the animal 60 and results in efficient presentation of the virus 30 to the immune system of the animal 60, with consequent enhanced immunogenicity of the virus 30. The present invention thus facilitates formation of a vaccine comprising the virus 30 wherein the immunological effectiveness of the vaccine may be exploited without increasing the dosage of the virus 30.

Since the virus 30 is unstable, the virus 30 will experience the spontaneous fission (i.e., falling apart) transformation 19 into viral fragments 41, 42, 43, 44, 45, and 46 respectively corresponding to the viral structural units 31, 32, 33, 34, 35, and 36. Each of the viral fragments 41, 42, 43, 44, 45, and 46 potentially evokes an immune response in the animal 60, since the blocker envelope 66 protects the virus 30 and enables the virus 30 to present itself to the immune system of the animal 60 for a period of time long enough for the immune system of the animal 60 to become immunologically sensitive to the virus 10. In particular, the "naked viral fragments" 41, 43, and 45 are immunogenic and will thus evoke an immune response from the animal 60, while the "enveloped viral fragments" 42, 44, and 46 are non-immunogenic and will thus not evoke an immune response from the animal 60. An "enveloped viral fragment" is a viral fragment that is enveloped by a blocker envelope of the type typified by the blocker envelope 66. For example, the enveloped viral fragments 42, 44, and 46 are enveloped by the blocker envelopes 67, 68, and 69, respectively, each having the same blocking characteristics described supra for the blocker envelope 66. As discussed supra, the immunogenicity of the virus 30 is defined to include the ability of the viral fragments 42, 44, and 46 to evoke an immune response from the animal 60. A "naked viral fragment" is a viral fragment that is not enveloped by a blocker envelope. The present invention significantly enhances the immunogenicity of the virus 30, because: (1) the blocker envelopes 66 increases the survival time of the virus 30 in the animal 60 (i.e., significantly extends the time interval during which the virus 30 presents itself to the immune system of the animal 60); and (2) most of the fragments resulting from fissioning of the virus 30 are naked viral fragments rather than enveloped viral fragments.

As explained supra, an immunogenicity, or an enhancement of immunogenicity, may be determined or confirmed by measurement of antibody formation by the animal 60 in response to presentation of the virus 30 to the immune system of the animal 60. Immunization by vaccine requires that the quantity of the virus 30 that is introduced into the animal 60 be sufficient to immunize the animal 60 against infection by the virus 30.

A vaccine that comprises a collection of such viruses 30 is characterized by retention or non-removal of a substantial portion of the viruses 30 until the animal 60 has become immunologically sensitive. Thus, a vaccine formed in accordance with the polymerated linker chemical of the present invention may be effectively used with a lower viral dosage than would be used by a vaccine of the related art.

FIGS. 1, 2, and 3 show "viral-physiological structures." A viral-physiological structure is defined herein as an organic structure that includes a virus, together with any animal that comprises the virus and with any chemical that is covalently bonded to the virus.

As discussed supra in conjunction with FIG. 3, the present invention uses a polymerated linker chemical 37 to generate the blocker envelope 66, which enables the virus 30 to present itself to the immune system of the animal 60 long enough for said immune system to become immunologically sensitive to the animal 60. The use of the blocker envelope 66 is non-specific as to the type of virus whose average survival time may be increased in accordance with the present invention for the purpose of increasing the immunogenicity of the virus 30. Any virus that can infect an animal (human or non-human) can have its survival time so increased in accordance with the present invention. FIG. 4 tabulates examples of viruses whose survival times can be increased in accordance with the present invention. Each listed virus in FIG. 4 is classified as to whether said listed virus is of human significance or of veterinary significance. A virus is of human significance if the virus is known to one of ordinary skill in the art as being capable of infecting a human animal. A virus is of veterinary significance if the virus known to one of ordinary skill in the art as being capable of infecting a non-human animal. The list of viruses in FIG. 4 is merely exemplary. Numerous viruses other than those listed in FIG. 4 can have its survival time increased in accordance with the present invention.

Figure 5:
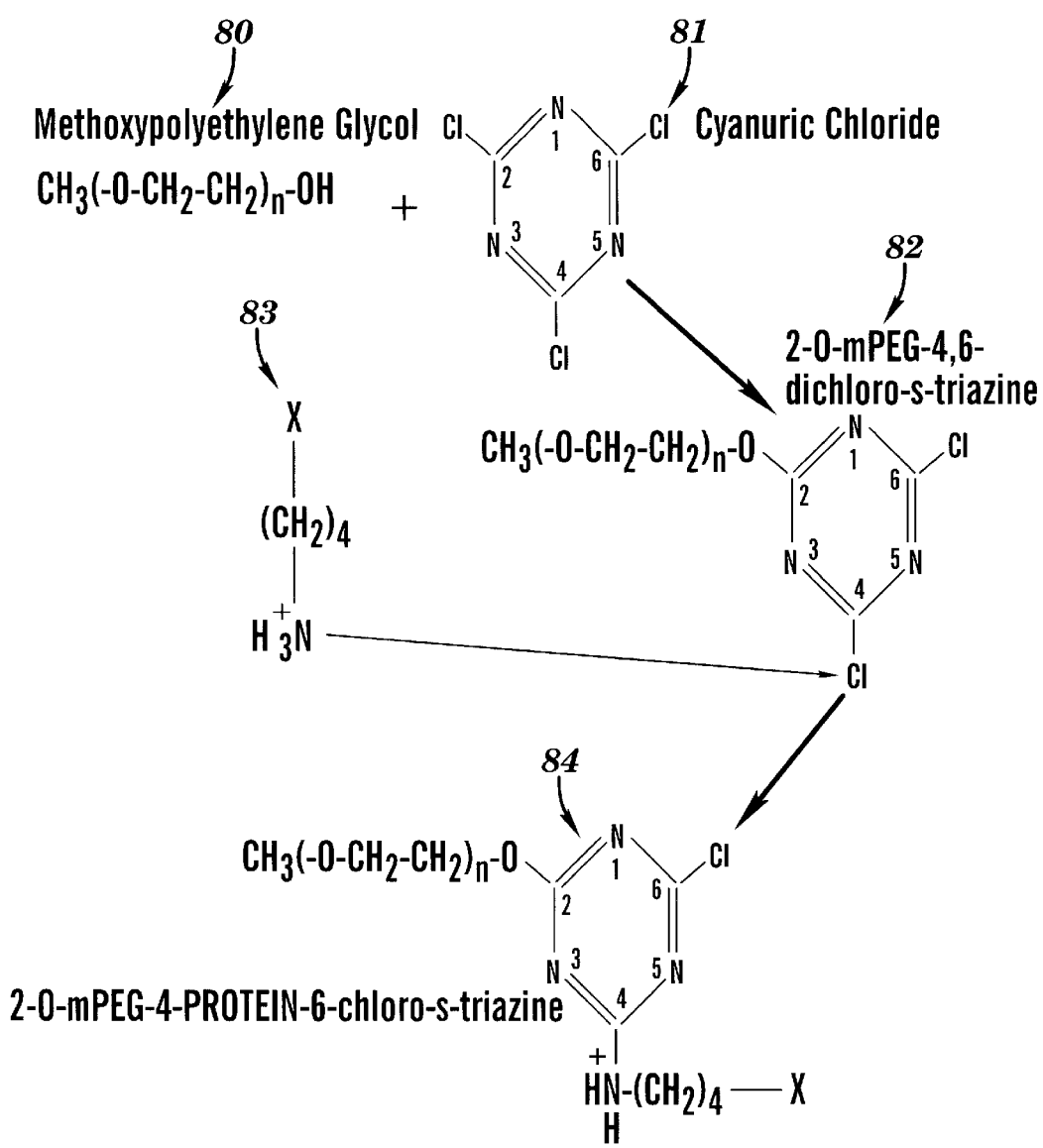
FIG. 5 depicts an exemplary chemistry of coupling a polymerated linker chemical to protein in the viral capsid of FIG. 1, in accordance with embodiments of the present invention.

FIG. 5 illustrates an exemplary chemistry of coupling the polymerated linker chemical, as depicted in FIG. 1 or FIG. 3, to a protein, in accordance with embodiments of the present invention. In FIG. 5, two chemical reactions are illustrated. In the first chemical reaction shown in FIG. 5, a polymer 80 reacts with a linker molecule 81 to form a polymerated linker chemical (PLC) 82 in which the polymer 80 is covalently bonded to the linker molecule 81. Specifically in FIG. 5, the polymer 80 is methoxypolyethylene glycol (mPEG) having the chemical structure of $CH_3(-O-CH_2-CH_2)_n-OH$ wherein $n \geq 2$. The linker molecule 81 is an alkyl halide (namely, cyanuric acid) and the resultant PLC 82 is 2-O-mPEG-4,6-dichloro-s-triazine. In the first chemical reaction, the hydroxyl group ($OH^-$) is a nucleophile that reacts generally with an alkyl halide (specifically, cyanuric chloride), resulting in displacement and release of the chlorine ion (CL⁻) in position 2 of the cyanuric chloride triazine ring as well as release of the hydrogen ion (H⁻) from the hydroxy group of the mPEG. The first chemical reaction may be implemented in any manner known to one of ordinary skill in the art such as in, inter alia, anhydrous benzene at a temperature of about 25° C. Formation of the PLC 82 of 2-O-mPEG-4,6-dichloro-s-triazine is well-known in the art and may be obtained commercially.

In the second chemical reaction shown in FIG. 5, a protein 83 reacts with the PLC 82 to form a protein-polymer complex 84. Specifically in FIG. 5, the protein 83 includes lysine, wherein $H_3N^+$—$(CH_2)_4$ is a portion of the lysine that reacts with the PLC 82, and wherein X represents a remaining portion of the protein 83 including a remaining portion of the lysine. The remaining portion of the lysine has a carbon atom covalently bonded to H, $H_3N^+$, and a carboxyl group. As shown in FIG. 5, a hydrolysis of the chlorine in position 4 of the cyanuric chloride triazine ring has replaced said chlorine in position 4 with the $H_3N^+$—$(CH_2)_4$ portion of the lysine of the protein 83, to form the protein-polymer complex 84. Specifically in FIG. 5, the protein polymer complex 84 is 2-O-mPEG-4-Y-6-chloro-s-triazine, wherein Y is the protein $H_3N^+$—$(CH_2)_4$-X. More generally, FIG. 5 shows generation of a PEG-conjugated protein with attachment of an activated PEG (e.g., the PLC 82) to an ε-amino group (e.g., the lysine or another amino acid such as arginine). The second chemical reaction may be implemented in an alkaline phosphate buffer (e.g., 50 mM of $K_2HPO_4$ and 105 mM of NaCl, wherein mM denotes millimoles). The second reaction can be efficiently accomplished in a wide range of media including, inter alia, saline, phosphate buffered saline, blood plasma, blood serum, albumin containing buffers, Hanks Balanced Salt Solution (HBSS), N-[2-hydroxyethyl]piperazine-N'-2-ethanesulfonic acid ("HEPES"), Roswell Park Memorial Institute 1640 ("RPMI 1640"), etc.

Time and temperature for performing the second reaction are very flexible. For example, a reaction between mPEG and amino acid of a viral capsid may be accomplished in 4 minutes or longer at 4° C. if the pH is about 9. If the pH is lower (e.g., about 8), the reaction may proceed at room temperature for a longer period (e.g., 60 minutes or longer) so that the virus is stressed by temperature and not stressed by harsh alkaline conditions. As to pH, it is useful to have a pH of about 8 when reacting mPEG with lysine. When reacting mPEG with a virus, weakly acidic to alkaline conditions should be used with a representative pH range of about 6.0 to about 9.0.

Effective doses of the PLC in the second reaction depend on several variables, including: linker chemistry, the polymer being used, surface area of capsid surfaces being modified, etc.

It should be noted that the chlorine in position 6 of the cyanuric chloride triazine ring is quite unreactive and thus unavailable to react with either an amino acid or with a second polymerated linker chemical.

FIG. 5 illustrates a mechanism of the covalent attachment of the polymerated linker chemical of cyanuric chloride coupled methoxypolyethylene glycol (mPEG) with viral capsid proteins, and potentially viral carbohydrates. Virtually all viruses can be similarly modified with only slight variations in pH, temperature and time. Indeed, the pH, time and temperature conditions at which the modification reaction can be done at are very malleable, thus making this invention applicable to a wide variety of virus types. Other polymers may be utilized instead of MPEG, such as, inter alia, polyethylene glycol, ethoxypolyethylene glycol, dextran, ficoll, and arabinogalactan. Other linker molecules may be utilized instead of cyanuric chloride, such as, inter alia, imidazolyl formate, succinimidyl succinate, succinimidyl glutarate, N-hydroxysuccinimide, 4-Nitrophenol, 2,4,5-trichlorophenol, and a chloroformate. FIG. 6 lists exemplary polymerated linker compounds (PLCs) that may be used with the present invention and associated targets that can be reacted with the PLCs. Most of the listed targets in FIG. 6 are proteins. The thiol groups in FIG. 6 include sulfhydryl groups which are protein components. Any of the PLCs that react with the hydroxyl group can be reacted with a carbohydrate. Note that the PLC of phospholipid PEG interacts with a lipid by intercalation rather than by covalent bonding.

The present invention has application to vaccines such that the vaccines would ordinarily be prepared in vitro but utilized in vivo. The present invention may be used for immunizing an animal, and also for research and testing of vaccines. Another way to utilize the present invention is to deliver a polymerated linker chemical into an animal that has, may have, or is thought to have, an already-present virus within the animal, wherein the polymerated linker chemical would envelop the already-present virus so as to enable the already-present virus to immunize the animal against any infection potentially transferrable to the animal from the already-present virus. Delivery of the polymerated linker chemical into the animal may be through (or into) the entry 63 into the animal 60 of FIG. 1, by any method or mechanism analogous to that described supra for causing which the virus 56 of FIG. 1 to enter the animal 60.

The present invention is illustrated by the following non-limiting example.

EXAMPLE

An experiment was conducted to test the extent to which a PEG modification of a virus enhances an immune response in mice, referenced against an immune response induced in the mice by a naked virus.

Simian Vacuolating Agent (SV40) viruses were covalently modified with a polymerated linker chemical of cyanuric chloride activated methoxypolyethylene glycol (CmPEG) at pH 8.0 in Minimal Essential Medium (MEM) (a Cellgro® cell media product by Mediatech, Inc.), supplemented with 5% fetal bovine serum (FBS) and MEM vitamins and mineral supplement. The CmPEG-SV40 viruses were covalently modified at room temperature for a period of either 30 minutes or 60 minutes. The CmPEG-SV40 viruses were then purified using a PEG-Dextran two-phase partitioning system. It should be noted that the SV40 virus has veterinary significance, but does not have human significance.

Naïve Balb/c mice (i.e., mice who have no preexisting antibodies to the SV40 virus) were then injected intraperitoneally: with saline (see FIG. 7) for control purposes; with purified naked SV40 virus (see FIG. 8) for reference case purposes; and with purified CmPEG-SV40 virus (see FIG. 9) for investigating enhancement of immunogenicity with respect to the mice. The virus concentration for each of FIGS. 8 and 9 was normalized to 1 microgram of viral protein.

At 4 weeks after the injections, the mice were sacrificed and mouse serum was collected. To assess in vivo antibody formation in the mice, purified SV40 was run on a 9% sodium dodecyl sulfate (SDS) polyacrylamide gel for Western Blot analysis. The gel proteins were transferred to nitrocellulose. Individual lanes of the nitrocelluose gel were then incubated with serum from the saline-injected mice, the naked SV40-injected mice, and the CmPEG-SV40-injected mice. Anti-SV40 antibodies present in the mouse serum were bound to the target antigen within the nitrocellulose strip. The presence of the mouse antibodies was then detected using horseradish peroxidase labeled rabbit anti-mouse IgG antibody. This reaction generates photons of lights which are recorded on x-ray film. The amount of antibody, as well as the diversity of the antibodies produced, were analyzed via densitometry of the x-ray film.

Figure 7:
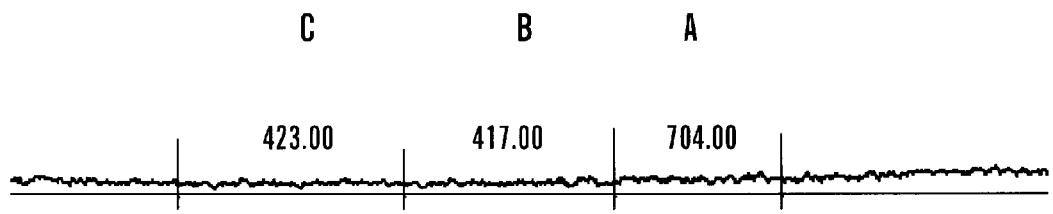
FIG. 7 depicts a densitometry curve showing antibody response levels in serum of mice that were injected with saline.
Figure 8:
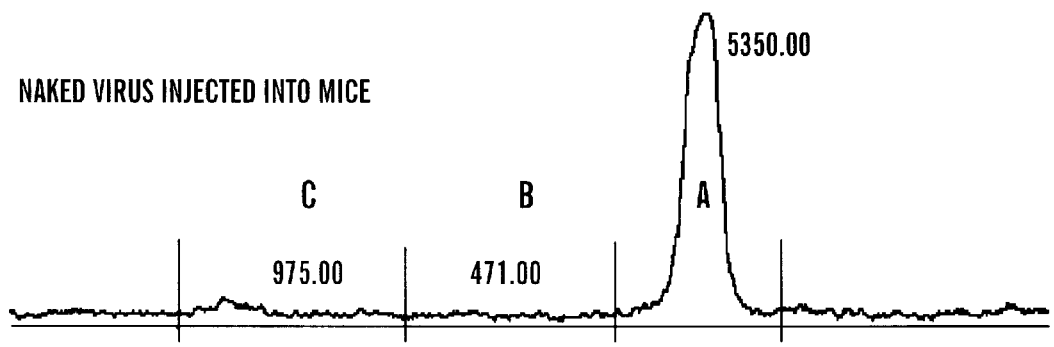
FIG. 8 depicts a densitometry curve showing antibody response levels in serum of mice that were injected with Simian Vacuolating Agent (SV40) virus.
Figure 9:
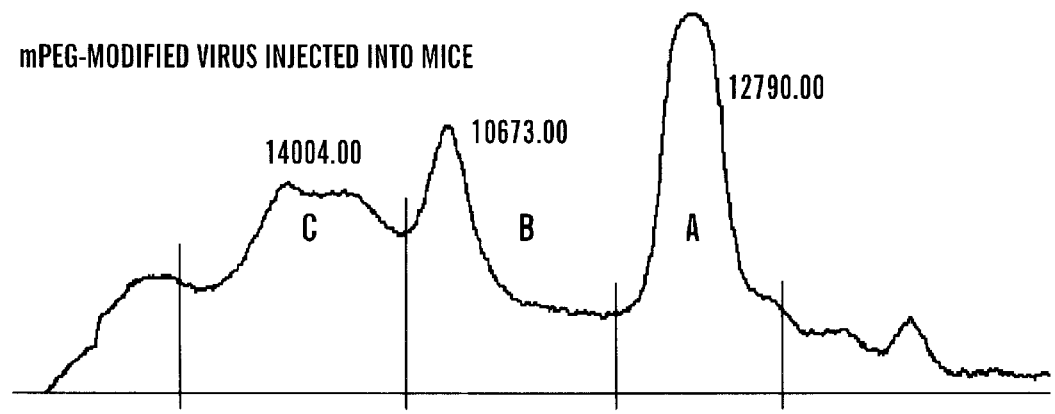
FIG. 9 depicts a densitometry curve showing antibody response levels in serum of mice that were injected with SV40 virus whose capsid was covalently bonded to a polymerated linker chemical.

The results are shown in FIGS. 7, 8, and 9. FIG. 7 depicts a densitometry curve showing antibody response levels in serum of mice that were injected with the saline. FIG. 8 depicts a densitometry curve showing antibody response levels in serum of mice that were injected with the naked SV40 virus. FIG. 9 depicts a densitometry curve showing antibody response levels in serum of mice that were injected with the CmPEG-SV40 virus.

FIG. 7 shows that the mice injected with saline made no SV40 antibodies, as evidenced by a lack of any significant peaks. In contrast, FIG. 8 shows that mice injected with naked SV40 virus demonstrated a potent immune response to the VP1 capsid protein (i.e., peak "A" in FIG. 8), but failed to elicit any other antibodies to viral proteins or other capsid components. Importantly, FIG. 9 shows that mice injected with CmPEG-SV40 virus not only had an enhanced antibody response to VP1 capsid protein (i.e., peak "A" in FIG. 9 as compared with peak "A" in FIG. 8), but also produced antibodies against a number of other viral proteins or components (i.e., peaks "B" and "C" in FIG. 9). The numbers associated with the A, B, and C portions of the densitometry curve of FIG. 9 (or FIG. 8) are areas under the A, B, and C portions of the densitometry curve of FIG. 9 (or FIG. 8) and respectively denote the relative abundances of the VP1 capsid protein, the viral component relating to B, and the viral component relating to C. Using the areas under the curves of peaks A, B, and C (after subtracting out the comparable areas in the saline-injected controls of FIG. 7 from FIGS. 8 and 9), and comparing FIG. 9 with FIG. 8, the following results are inferred. First, mPEG-modification increases the antibody response in the VP1 capsid protein by a factor of 2.4 (i.e., [12790-704]/[5350-704]). Second, the antibody response to viral protein B is increased by a factor of 189 (i.e., [10673-417]/[471-417]) for the CmPEG-SV40-injected virus as compared with the naked SV40-injected virus. Third, the antibody response to viral protein C is increased by a factor of 25 (i.e., [14004-423]/[975-423]) for the CmPEG-SV40-injected virus as compared with the naked SV40-injected virus.

The results of this example demonstrate a highly significant increase in immunogenicity (relative to mice) of the CmPEG-SV40 modified virus relative to the naked SV40 virus. While this test utilized MPEG as a polymer in the polymerated linker chemical, any other polymer discussed herein could have been used instead of MPEG. Similarly, while this test utilized cyanuric chloride as a linker molecule in the polymerated linker chemical, any other linker molecule discussed herein could have been used instead of cyanuric chloride.

While particular embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A method for enhancing an animal's immune response against a virus associated with a viral disease of said animal, comprising:

protecting a naked virus with a polymer covalently attached to a linker molecule covalently bonded to the capsid of the naked virus, wherein the polymer is polyethylene glycol, methoxypolyethylene glycol, or ethoxypolyethylene glycol, and wherein said polymer-protected virus is more immunogenic with respect to the animal than is the unprotected naked virus; and introducing the polymer-protected virus into the animal in an amount sufficient to induce an immune response against the virus.

2. The method of claim 1, wherein the animal is a human animal.

3. The method of claim 1, wherein the animal is a veterinary animal.

4. The method of claim 1, wherein introducing the polymer-protected virus into the animal comprises introducing the polymer-protected virus into the animal through a mouth of the animal.

5. The method of claim 1, wherein introducing the polymer-protected virus into the animal comprises introducing the polymer-protected virus into the animal through a nose of the animal.

6. The method of claim 1, wherein introducing the polymer-protected virus into the animal comprises introducing the polymer-protected virus into the animal by needle injection.

7. The method of claim 1, wherein the animal is a female animal, and wherein introducing the polymer-protected virus into the animal comprises introducing the polymer-protected virus into the animal through a vagina of the animal.

8. The method of claim 1, wherein the linker molecule is selected from the group consisting of cyanuric chloride, imidazolyl formate, succinimidyl succinate, succinimidyl glutarate, N-hydroxysuccinimide, 4-Nitrophenol, 2,4,5-trichlorophenol, and a chloroformate.

9. The method of claim 1, wherein covalently bonding the linker molecule to the capsid includes covalently bonding the linker molecule to an amino acid at the capsid.

10. The method of claim 1, wherein covalently bonding the linker molecule to the capsid includes covalently bonding the linker molecule to lysine group at the capsid.

11. The method of claim 1, wherein covalently bonding the linker molecule to the capsid includes covalently bonding the linker molecule to a carbohydrate at the capsid.

12. The method of claim 1, wherein covalently bonding the linker molecule to the capsid includes covalently bonding the linker molecule to a sulfhydryl group at the capsid.

13. The method of claim 1, wherein covalently bonding the linker molecule to the capsid comprises:

providing a polymerated linker chemical that comprises the polymer covalently bonded to the linker molecule; and chemically reacting the polymerated linker chemical with the capsid to covalently bond the linker molecule to the capsid.

14. The method of claim 1, wherein the immune response immunizes the animal against infection by the virus.

15. The method of claim 14, wherein the animal is a human animal.

16. The method of claim 14, wherein the animal is a veterinary animal.

17. The method of claim 14, wherein the linker molecule is selected from the group consisting of cyanuric chloride, imidazolyl formate, succinimidyl succinate, succinimidyl glutarate, N-hydroxysuccinimide, 4-Nitrophenol, 2,4,5-trichlorophenol, and a chloroformate.

18. The method of claim 14, wherein the linker molecule is covalently bonded to an amino acid at the capsid.

19. The method of claim 14, wherein the linker molecule is covalently bonded to a lysine group at the capsid.

20. The method of claim 14, wherein the linker molecule is covalently bonded to a sulfhydryl group at the capsid.

21. A method, comprising:

covalently bonding a linker molecule to a carbohydrate at the capsid of a naked virus, wherein a polymer is covalently attached to the linker molecule to form a polymer-protected virus, and wherein an immunogenicity of the polymer-protected virus with respect to an animal exceeds an immunogenicity of the naked virus with respect to the animal.

22. A structure, comprising:

a linker molecule covalently bonded to the capsid of a naked virus, wherein a polymer is covalently attached to the linker molecule to form a polymer-protected virus, wherein the immunogenicity of the polymer-protected virus with respect to an animal exceeds the immunogenicity of the naked virus with respect to to the animal, wherein the naked virus has human significance, and wherein the polymer is selected from the group consisting of polyethylene glycol, methoxypolyethylene glycol, and ethoxypolyethylene glycol.

23. The structure of claim 22, wherein the linker molecule is selected from the group consisting of cyanuric chloride, imidazolyl formate, succinimidyl succinate, succinimidyl glutarate, N-hydroxysuccinimide, 4-Nitrophenol, 2,4,5-trichlorophenol, and a chloroformate.

24. The structure of claim 22, wherein the linker molecule is covalently bonded to an amino acid at the capsid.

25. The structure of claim 22, wherein the linker molecule is covalently bonded to a lysine group at the capsid.

26. The structure of claim 22, wherein the linker molecule is covalently bonded to a sulfhydryl group at the capsid.

27. A structure, comprising:

a linker molecule covalently bonded to a carbohydrate at the capsid of a naked virus, wherein a polymer is covalently attached to the linker molecule to form a polymer-protected virus, wherein an immunogenicity of the polymer-protected virus with respect to an animal exceeds an immunogenicity of the naked virus with respect to the animal.

28. A structure, comprising:

a linker molecule covalently bonded to the capsid of a naked virus, wherein a polymer is covalently attached to the linker molecule to form a polymer-protected virus, wherein the polymer has a long chain length that causes the immunogenicity of the polymer-protected virus with respect to a given animal to exceed the immunogenicity of the virus with respect to the given animal, wherein the naked virus has human significance, and wherein the polymer is selected from the group consisting of polyethylene glycol, methoxypolyethylene glycol, and ethoxypolyethylene glycol.

29. A structure comprising:

a linker molecule covalently bonded to the capsid of a naked virus, wherein a polymer is covalently attached to the linker molecule to form a polymer-protected virus, wherein a camouflaging of a charge site at the capsid by the polymer causes the immunogenicity of the polymer-protected virus with respect to a given animal to exceed the immunogenicity of the virus with respect to the given animal, wherein the naked virus has human significance.

30. The structure of claim 29, wherein the linker molecule is selected from the group consisting of cyanuric chloride, imidazolyl formate, succinimidyl succinate, succinimidyl glutarate, N-hydroxysuccinimide, 4-Nitrophenol, 2,4,5-trichlorophenol, and a chloroformate.

31. The structure of claim 29, wherein the linker molecule is covalently bonded to an amino acid at the capsid.

32. The structure of claim 29, wherein the linker molecule is covalently bonded to a lysine group at the capsid.

33. The structure of claim 29, wherein the linker molecule is covalently bonded to a sulfhydryl group at the capsid.

34. The structure of claim 29, wherein the polymer is selected from the group consisting of polyethylene glycol, methoxypolyethylene glycol, ethoxypolyethylene glycol, dextran, ficoll, and arabinogalactan.

* * * * *